US00PP31377P2

(12) United States Plant Patent
de Groot

(10) Patent No.: US PP31,377 P2
(45) Date of Patent: Jan. 21, 2020

(54) ***ROSA* PLANT NAMED 'RUIRCO120A'**

(50) Latin Name: *Rosa hybrida*
Varietal Denomination: RUIRCO120A

(71) Applicant: Hendrikus de Groot, Amstelveen (NL)

(72) Inventor: Hendrikus de Groot, Amstelveen (NL)

(73) Assignee: De Ruiter Intellectual Property, BV (NL)

( * ) Notice: Subject to any disclaimer, the term of this patent is extended or adjusted under 35 U.S.C. 154(b) by 0 days.

(21) Appl. No.: 16/350,981

(22) Filed: Feb. 7, 2019

(51) Int. Cl.
*A01H 5/02* (2018.01)
*A01H 6/74* (2018.01)

(52) U.S. Cl.
USPC ..... Plt./151
CPC ..... *A01H 6/74* (2018.05)

(58) Field of Classification Search
USPC ..... Plt./151, 150
CPC ..... A01H 5/0222
See application file for complete search history.

*Primary Examiner* — Kent L Bell
(74) *Attorney, Agent, or Firm* — Cassandra Bright

(57) ABSTRACT

A new and distinct hybrid *Rosa* cultivar named 'RUIRCO120A' is disclosed, characterized by large, double red flowers with a light floral fragrance. Plants are upright, and exhibit good resistance to blackspot diseases. The new variety is a *Rosa*, normally produced as an outdoor garden or container plant.

3 Drawing Sheets

Latin name of the genus and species: *Rosa hybrida.*
Variety denomination: 'RUIRCO120A'.

BACKGROUND OF THE INVENTION

The new *Rosa* cultivar is a product of a planned breeding program conducted by the inventor. The objective of the breeding program was to produce improved rose varieties. The cross resulting in this new variety was made during Spring of 2002, by the inventor at a research nursery in Hazerswoude, The Netherlands.

The seed parent is the variety *Rosa* 'Flower Carpet Red', U.S. Plant Pat. No. 10,084. The pollen parent is the unpatented *Rosa* 'TANanaistrua'. The new variety was selected in June 2003 by the inventor at the same research nursery in Hazerswoude, The Netherlands. The inventor continued observing characteristics of the new variety for several years, in the controlled conditions of the research nursery.

Asexual reproduction of the new cultivar has been performed by vegetative softwood cuttings. This was first performed at a greenhouse in Hazerswoude, The Netherlands, in August 2003, and has shown that the unique features of this cultivar are stable and reproduced true to type in successive generations.

SUMMARY OF THE INVENTION

The cultivar 'RUIRCO120A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRCO120A' These characteristics in combination distinguish 'RUIRCO120A' as a new and distinct *Rosa* cultivar:

1. Good fragrance.
2. Deep red flower color.

PARENTAL COMPARISON

Plants of the new cultivar 'RUIRCO120A' are similar to plants of the seed parent, in most horticultural characteristics, however, plants of the new cultivar 'RUIRCO120A' differ in the following:

1. The new variety has a deeper red flower color, while the seed parent has lighter red flowers.
2. New cultivar has no fading in the center of its flowers, while the parent's flowers fade to white in the center.

Plants of the new cultivar 'RUIRCO120A' are similar to plants of the pollen parent in most horticultural characteristics, however, plants of the new cultivar 'RUIRCO120A' differs in the following;

1. New cultivar has no fading in the center of its flowers, while the parent's flowers fade to white in the center.

COMMERCIAL COMPARISON

Plants of the new cultivar 'RUIRCO120A' can be compared to the commercial variety *Rosa* 'Meiboulka', U.S. Plant Pat. No. 19,258. These varieties are similar in most horticultural characteristics, however 'RUIRCO120A' differs in the following:

1. This new cultivar has double flowers; this comparator has single flowers.
2. The new variety has red flowers, while this comparator has red-magenta flowers.
3. The new variety has lighter green foliage than the comparator.

BRIEF DESCRIPTION OF THE PHOTOGRAPHS

The accompanying photograph in FIG. 1 illustrates in full color a typical plant of 'RUIRCO120A' in a 2 gallon container grown in Grand Haven, Mich. in a polyhouse. Plants in FIG. 1 are approximately 2 to 3 years old.

Figure 1:
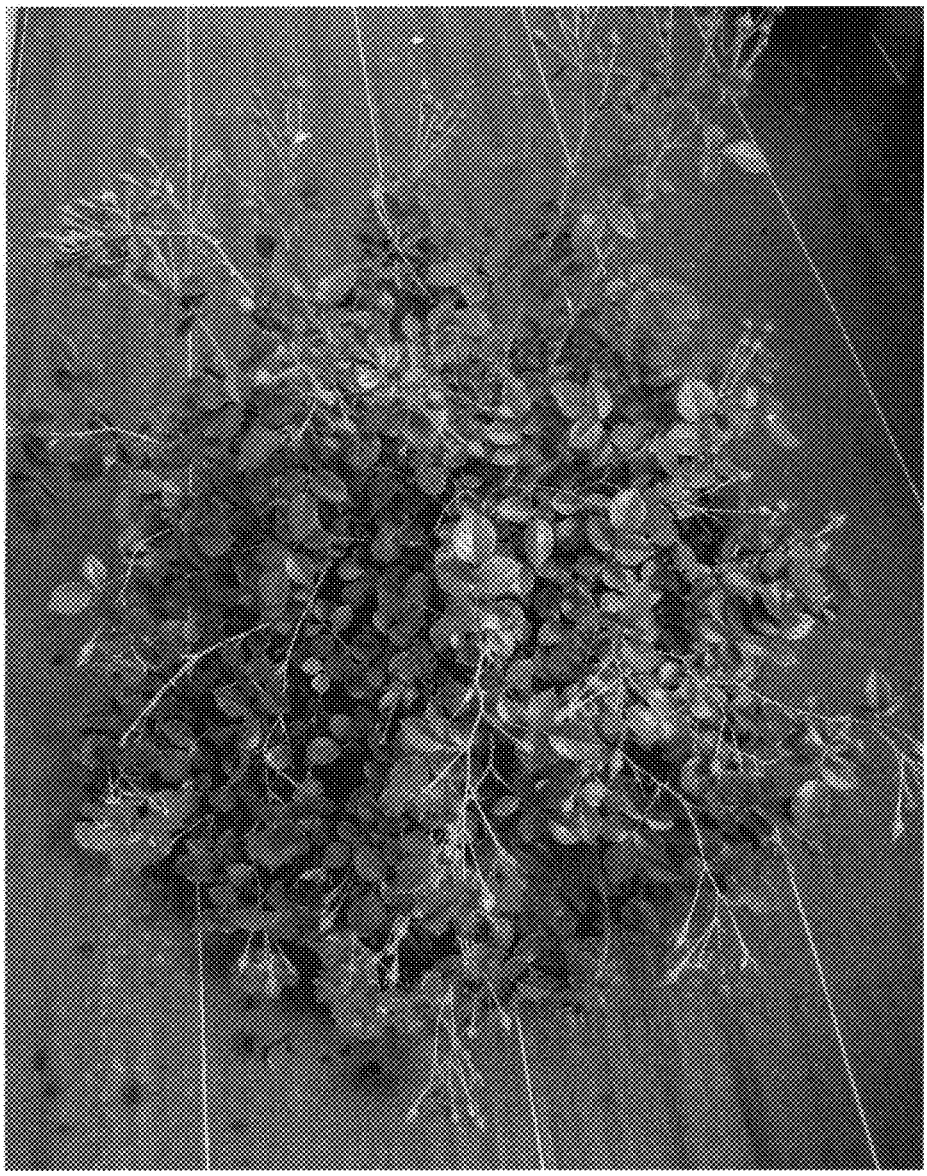
Figure 2:
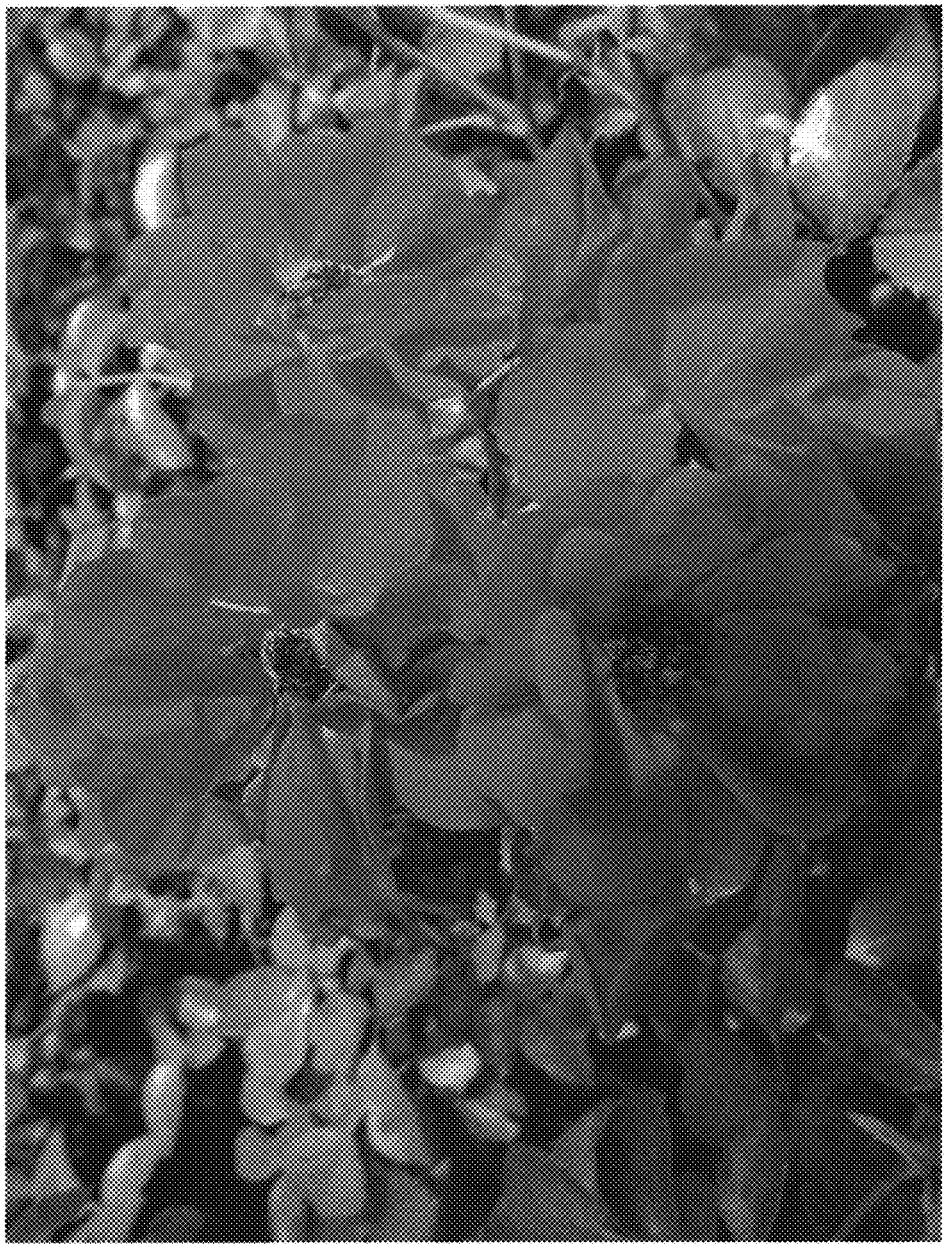
FIG. 2 illustrates a close up view of the flowers.
Figure 3:
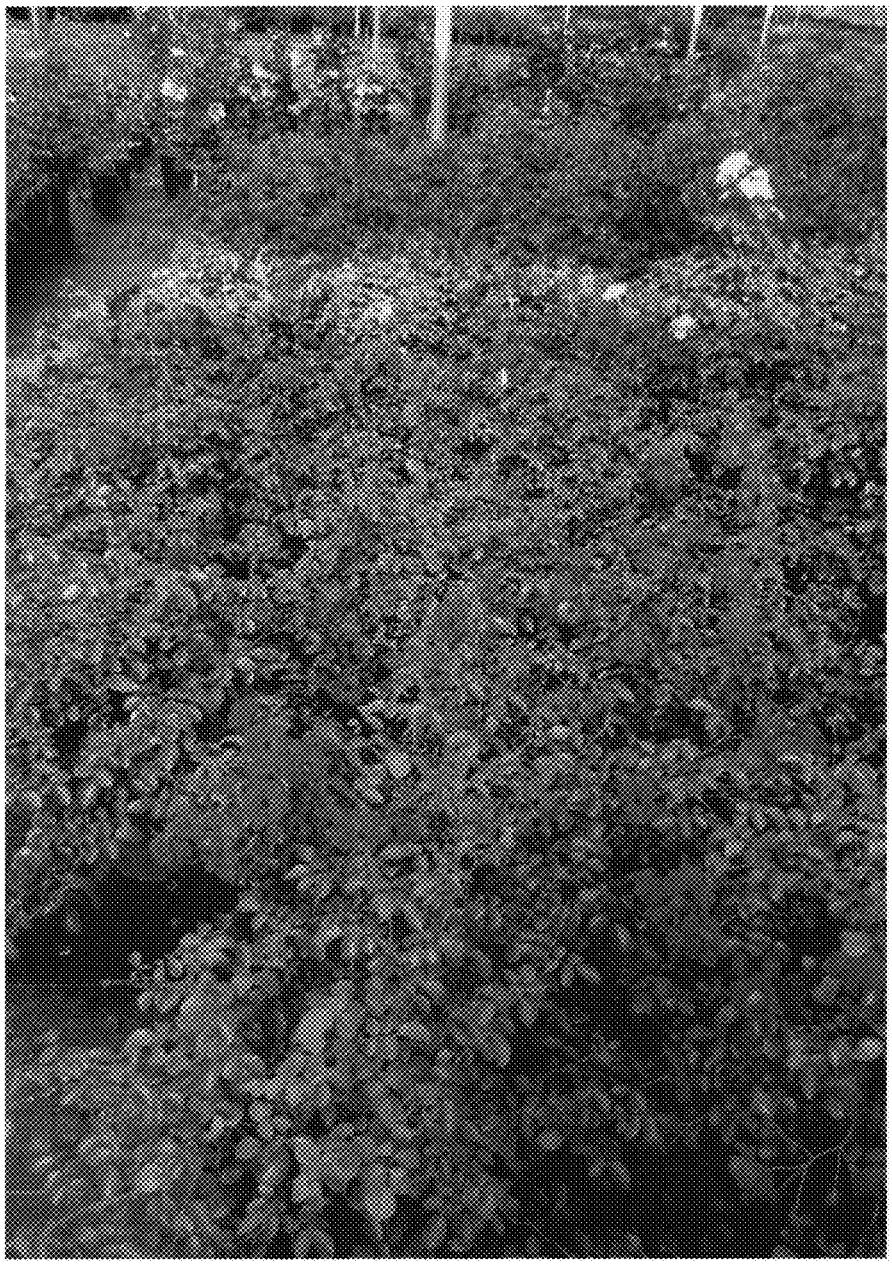
FIG. 3 illustrates a mature plant during Summer of 2018.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRCO120A' plants grown outdoors, in Hazerswoude, The Netherlands. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'RUIRCO120A'.

Market classification: Floribunda garden rose.

PROPAGATION

Time to initiate roots: 30 days at approximately 20° C.

Time to produce a rooted cutting: 120 days at approximately 20° C.

PLANT

Age of plant described: 2-3 years.

Container size: 1, 2, 3, 5 gallon pots.

Height: 35 cm.

Plant spread: 121 cm.

Rootstock: Own root.

Growth rate: Good.

Branching habit: Very outwardly/horizontally branched, most branches 75° from center. Some branches upright.

Length of primary lateral branches: 50 cm.

Diameter of lateral branches: 4 mm.

Quantity lateral branches: 18.

Internode length: 2.25 cm.

Stem:

- *Appearance*.—Round with thorns.
- *Aspect*.—20-180 degrees.
- *Strength*.—Moderate.
- *Color*.—RHS Green 143C.
- *Pubescence*.—Yes.

Thorns:

- *Number per linear centimeter*.—2.
- *Shape*.—Narrow deltate, bent downward.
- *Apex*.—Acicular.
- *Height*.—5 mm.
- *Color*.—Immature: RHS Yellow-Orange 18D with Red 47A. Mature: RHS Red 47A.

FOLIAGE

Leaf:

- *Arrangement*.—Opposite.
- *Quantity*.—Average 11 per lateral branch.
- *Average length*.—8.5 cm.
- *Average width*.—6 cm.

Leaflet:

- *Quantity*.—5 to 7 per leaf.
- *Terminal length*.—3.25 cm.
- *Terminal width*.—2.25 cm.
- *Lateral length*.—3 cm.
- *Lateral width*.—1.75 cm.
- *Shape*.—Obovate.
- *Apex*.—Acute.
- *Base*.—Rounded.
- *Margin*.—Serrate.
- *Pubescence*.—None.
- *Texture*.—Smooth, glossy.
- *Color*.—Young foliage upper side: RHS Green 137A. Young foliage under side: RHS Green 138B. Mature foliage upper side: RHS Green 138A. Mature foliage under side: RHS Green 138B.
- *Venation*.—Pattern: Pinnate. Color, upper side: RHS Yellow-Green N144D. Color, under side: RHS Green 139D.

Petiole:

- *Leaf petiole length*.—5 mm.
- *Leaf petiole diameter*.—2 mm.
- *Leaflet petiole length*.—<1 mm.
- *Leaflet petiole diameter*.—1 mm.
- *Leaf petiole texture*.—Micro-thorns.
- *Leaflet petiole texture*.—Smooth.
- *Leaf petiole color, upper surface*.—RHS Green 139D.
- *Leaf petiole color, lower surface*.—RHS Green 139D.
- *Leaflet petiole color, upper surface*.—RHS Red-Orange 34A.
- *Leaflet petiole color, lower surface*.—RHS Green 139D.

Stipule:

- *Quantity*.—2.
- *Shape*.—Falcate.
- *Apex*.—Linear/Acicular.
- *Base*.—Fused along petiole, base slightly truncate.
- *Margin*.—Ciliate.
- *Length*.—1.5 cm.
- *Width*.—3 mm.
- *Texture, upper surface*.—Ciliate.
- *Texture, lower surface*.—Smooth.
- *Color, upper surface*.—RHS Green 139C.
- *Color, lower surface*.—RHS Green 139C.

FLOWER

Natural flowering season: Spring to Summer.

Flower type and habit: Double, occurring in sprays.

Quantity of flowers: 3 per spray.

Sprays per lateral stem: 1.

Flower:

- *Shape*.—Double whorl.
- *Diameter*.—5.5 cm.
- *Height*.—2 cm.
- *Aspect*.—Outwards and slightly upwards.
- *Persistent or self-cleaning*.—Self-cleaning.
- *Fragrance*.—Pleasant, floral.

Peduncle:

- *Length*.—4 cm.
- *Diameter*.—3 mm.
- *Angle*.—15-180 degrees.
- *Strength*.—Flexible.
- *Texture*.—Micro-thorns.
- *Color*.—RHS Green 143C.

Petals:
*Arrangement*.—Double whorl.
*Appearance*.—Intensely vibrant.
*Petal quantity*.—15.
*Fused*.—No.
*Length*.—2.5 cm.
*Width*.—2 cm.
*Shape*.—Obovate.
*Margin*.—Entire.
*Apex*.—Retuse.
*Base*.—Obtuse.
*Texture*.—Smooth, silky.
*Color*.—When opening: Upper surface: RHS Red 53A. Lower surface: RHS Red 53A. Fully opened: Upper surface: RHS Red N45A. Lower surface: RHS Red N45A.

Petaloids:
*Appearance*.—Small, curved.
*Arrangement*.—Whorled.
*Number*.—4.
*Shape*.—Irregular.
*Margin*.—Entire.
*Length*.—1.5 cm.
*Width*.—8 mm.
*Color, immature*.—RHS Red N45A.
*Color, mature*.—RHS Red N45A.

Bud:
*Shape*.—Ovate.
*Length*.—2 cm.
*Diameter*.—1.5 cm.
*Color*.—RHS Red 53A.

Sepals:
*Quantity*.—5.
*Arrangement*.—Whorled.
*Length*.—1.5 cm.
*Width*.—7.5 mm.
*Shape*.—Acuminate.
*Apex*.—Acuminate.
*Base*.—Truncate.
*Margin*.—Pubescent.
*Color*.—Immature, Upper Side: RHS Green 143C. Immature, Under Side: RHS Green 143B. Mature, Upper Side: RHS Green 143C. Mature, Under Side: RHS Green 143B.
*Texture*.—Smooth, pubescent, all surfaces.

Peduncle:
*Length*.—4 cm.
*Diameter*.—3 mm.
*Angle*.—15-180 degrees.
*Strength*.—Flexible.
*Texture*.—Micro-thorns.
*Color*.—RHS Green 143C.

Receptacle:
*Length*.—3.5 cm.
*Width*.—4.0 cm.
*Shape*.—Obovate.
*Texture*.—Smooth.
*Color*.—RHS Green 140A.

REPRODUCTIVE ORGANS

Stamens:
*Quantity*.—Average 100.
*Filament length*.—Average 8 mm.
*Filament color*.—RHS Red 54D.

Anthers:
*Length*.—1 mm.
*Shape*.—Club-like.
*Color*.—RHS Yellow-Orange 17A.
*Pollen*.—Color: RHS Yellow-Orange 17A. Quantity: Moderate.

Pistil:
*Number*.—20.
*Length*.—5-7 mm.

Stigma:
*Shape*.—Clustered.
*Color*.—RHS Yellow 13B.

Style:
*Length*.—Average 3 mm.
*Color*.—RHS Red 54D.

OTHER CHARACTERISTICS

Seeds and fruits: Not observed.

Disease/pest resistance: Good overall disease resistance to normal pests and diseases typical of garden roses. Very good resistance to blackspot diseases.

What is claimed is:

1. A new and distinct hybrid cultivar of *Rosa* plant named 'RUIRCO120A' as herein illustrated and described.

* * * * *